United States Patent

Bakels

[11] 4,252,054
[45] Feb. 24, 1981

[54] DENTAL CLEAN AIR DEVICE

[76] Inventor: Marinus Bakels, 3896 Burns Rd., Palm Beach Gardens, Fla. 33410

[21] Appl. No.: 938,133

[22] Filed: Aug. 30, 1978

[51] Int. Cl.$^2$ ............................................. F23J 11/00
[52] U.S. Cl. ............................. 98/115 R; 55/385 A; 312/209; 422/104
[58] Field of Search ............... 422/104; 55/385 A; 98/36, 115 R, 115 LH; 312/209

[56] References Cited

U.S. PATENT DOCUMENTS

| | | | |
|---|---|---|---|
| 3,041,957 | 7/1932 | Liptay | 98/115 LH |
| 3,336,855 | 8/1967 | Messina | 98/115 LH |
| 3,729,905 | 5/1973 | Diccianni | 98/115 LH |
| 3,768,970 | 10/1973 | Malmin | 55/279 |
| 3,820,536 | 6/1974 | Anspach, Jr. et al. | 55/385 A |
| 4,016,809 | 4/1977 | Austin | 98/115 LH |

*Primary Examiner*—Ronald C. Capossela

[57] ABSTRACT

A dental clean air cabinet is provided with a hood over a table top opening for directing flow thereto, said opening being covered by a heavy supporting screen. The inner portion of the cabinet is divided into two compartments, one compartment containing a blower, or turbine, providing suction action for drawing contaminated air into said hood through said screen and directing it into said other compartment, said other bottom compartment having a large filter outlet for filtering said contaminated air and directing clean air therefrom, said table top having a receptacle therein for plugging in an amalgam mixing device which can be placed on the heavy supporting screen for operation. The cabinet includes a switch for turning said blower on and off and a combination switch and timer for directing current to said receptacle for operating said amalgam mixing device, said hood having a door for controlling flow into an out of said hood. A microswitch is electrically connected in the system so that the amalgam mixing device will not operate until the door is closed. A controllable oral cavity collector is also connected to said cabinet having a second suction device located in said one compartment.

9 Claims, 2 Drawing Figures

DENTAL CLEAN AIR DEVICE

BACKGROUND OF THE INVENTION

In performing dental operations, the breathing and air/water input produced by high speed dental and ultrasonic scaling equipment produces a large aerosol escapement, and this mist/particle combination is directed into the area of the operator's face, setting forth the threat of contamination or infection with regard to the dental operator and others. The above escapement can include removed solid tooth structure, decomposed organic tooth structure, bacteria laden compressed air and water, atomized blood and atomized saliva. Other hazards in a dental operation are (1) mercury vapors caused by mixing amalgam and spillage; and (2) the exhausting gas used as an anesthetic. The following prior art is known to Applicant: U.S. Pat. No. 3,768,970 and U.S. Pat. No. 3,820,536.

SUMMARY OF THE INVENTION

It is a general object of this invention to provide a dental clean air device for controlling environmental problems in a dental operating room.

It is an object of this invention to use an oral cavity collector to directly collect the breath and debris exhausted from a patient's mouth and suck it into the dental device where it is filtered to trap undesirable particles, vapors, and bacteria. Clean air is then directed back into the room.

Another object of the invention is to provide a hooded chamber connected with said dental device for mixing mercury concentrated amalgam. Mercury vapors are withdrawn from said chamber and filtered to prevent mercury vapor concentrate from entering the environment.

A further object of the invention is to provide a dental clean air device having two suction sources; one for ambient air and mercury vapors, and a second one for a direct oral cavity collector for bacteria and nitrous oxide or anesthetic gases.

Another object of the invention is to provide a plurality of filters on the dental clean air device; a high efficiency air filter for trapping the bacteria and cleaning particulate matter from the environment; a charcoal filter to trap mercury vapors; and a charcoal filter to trap nitrous oxide gases.

It is a further object of the invention to provide in a dental clean air cabinet a chamber wherein an amalgam mixing device can be placed for operation when desired and to control the closing of said chamber with the operation of said amalgam mixing device.

DESCRIPTION OF THE PREFERRED EMBODIMENT

Figure 1:
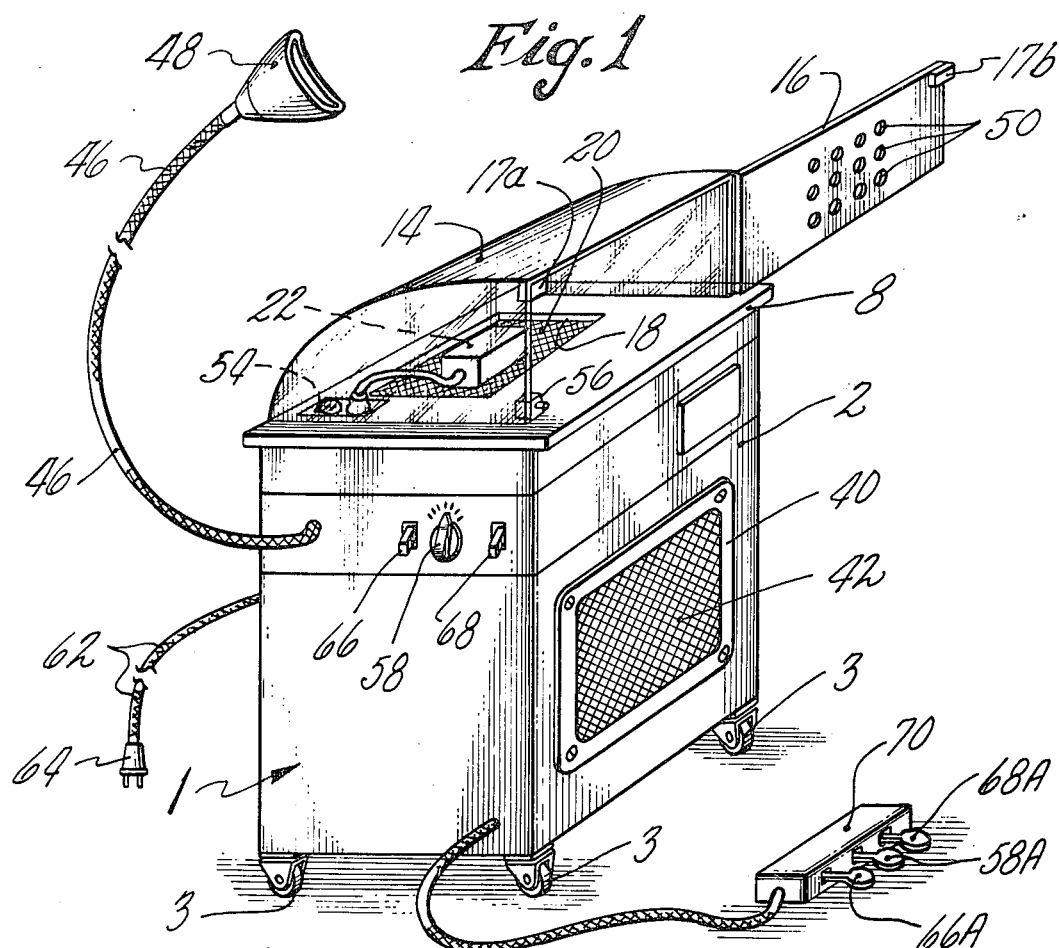
FIG. 1 is a front perspective view of a dental clean air device.
Figure 2:
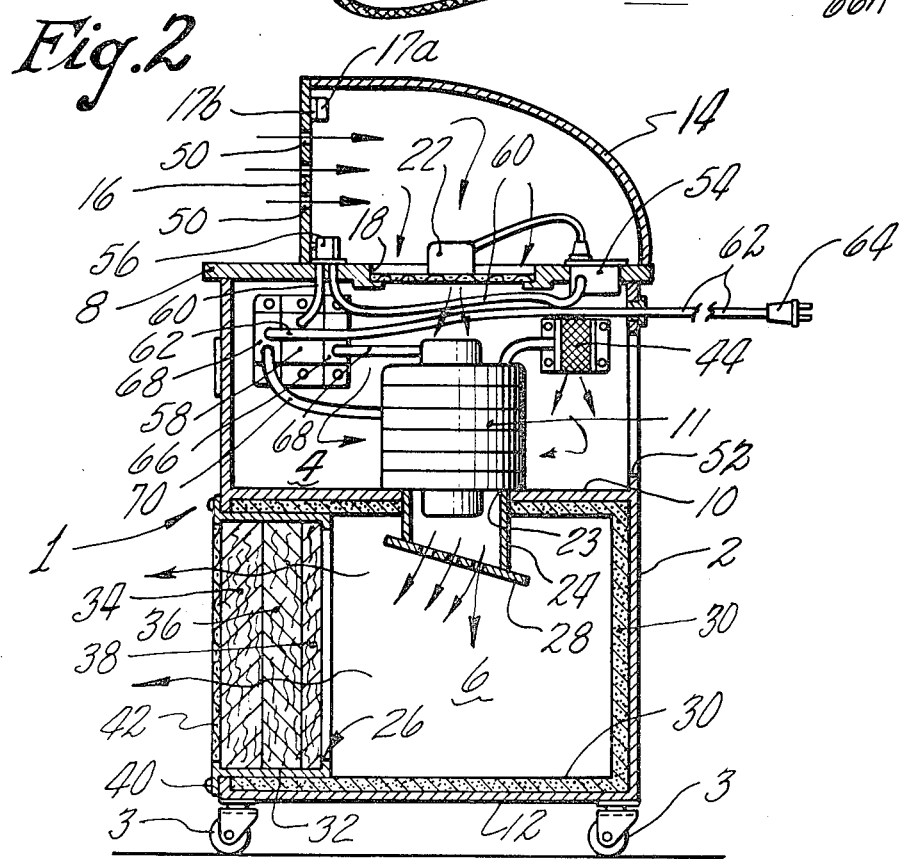
FIG. 2 is a section taken through the center of the device of FIG. 1.

As illustrated in FIG. 1, a dental clean air device 1 is shown as a cabinet 2 mounted on wheels 3 for ease of movement in a dental operating room. The cabinet 2 is shown having a box shape. The interior of the box-shape cabinet 2 is formed of two compartments, 4 and 6. The top of the cabinet has a table top 8 fixed thereto, while a partition 10 divides the compartments 4 and 6 and the bottom is closed by a plate 12. The table top has a hood 14 placed thereon, covering most of the table top 8, said hood 14 having a door 16 for providing an enclosed chamber. The hood may be made of a transparent material, such as plexiglass, or opaque material, such as sheet metal. The table top 8 has an opening 18 therein, under said hood 14, with a heavy screen 20 fixed therein for supporting an amalgam mixing device 22 in a manner as will be hereinafter described. The door has a magnetic holding device 17 with one part 17a on the hood 14 and another part 17b on the door. Other known holding devices can be used.

The opening 18 in the table top 8 opens into the compartment 4. This compartment 4 contains the suction equipment for operating the device. A large blower, or turbine, 11, is mounted in compartment 4 with its inlet positioned below the heavy screen 20 to suck, or draw, the gases therefrom and its outlet is directed into an opening 23 in the partition 10. A conduit 24 is positioned in the opening 23 and extends into the compartment 6 which directs the flow to a filter unit 26. A plate 28, having a plurality of pores therein, is fixed over the end of conduit 24 extending into the chamber 6 to act as a diffuser. A lead-foam insulation 30 is provided around the inside of the compartment 6. A second suction producing device 44 is located on a wall in compartment 4 and has an oral cavity collecting hose 46 connected to the suction inlet thereof. An oral cavity collector 48, contoured as a funnel, is placed on the free end of the collecting hose 46 so that it can be conveniently placed near the area being worked on by the dental operator. The gas and particles are drawn in through the oral cavity collector 48, pulled through the collecting hose 46 and directed through the outlet of the suction producing device 44 into the compartment 4. It is then drawn through the suction producing device 11 into the compartment 6.

The filter unit 26 includes a housing 32 having three filters, 34, 36, and 38 therein. These three filters 34, 36 and 38, are held between forward and rearward inwardly extending flanges on said filter unit 26. The filter 38 is a high efficiency air filter for trapping bacteria and particulate matter from the environment; filter 36 is a charcoal filter of the type to trap mercury vapors; and filter 34 is a charcoal filter of the type to trap nitrous oxide gases. The three filters may be held therein by any means desired. An external flange 40 around the forward part of the filter device engages the front of the cabinet and it is fixed thereto by conventional bolts. A decorative screen 42 is mounted in the front opening covering the filter unit 26.

As mentioned hereinbefore, a heavy screen 20 is fixed in opening 18 to support an amalgam mixing device 22 so that any mercury vapors caused by mixing an alloy of mercury with another metal, such as silver, will be drawn downwardly through the screen by the suction created by the blower 11 where it is directed to the filter unit 26. It is also noted that any spillage can also pass through the screen so that the vapors passing through will also be drawn through the clean air device. The spillage can be collected and removed from the compartment 4. The door 16 can be provided with a plurality of openings 50, or a space provided between the bottom of the door 16 and the table top 8, to permit air to be drawn into the hood to permit flow downwardly through the screen 20. An opening 52 can be provided at the rear of the compartment 4 to prevent excessive back pressure on the motor for the blower, or turbine, 11 when the door 16 is closed. The opening 17 could be provided with a manual slide cover to control the size of opening 52 as is desired to control the amount of flow through the closed hood.

The electric wiring system for the device is set forth as follows: A plug receptacle 54 is located in the top of table 8 under the hood 14. This receptacle is in turn electrically connected by a conduit 60 through a microswitch 56 to a combination switch and timer 58. The microswitch 56 is positioned at the forward edge of the hood adjacent the side opposite the hinge for door 16 and the combination switch and timer 58 is located on the same side of the cabinet 2. This microswitch 56 is normally open and when door 16 is closed, it closes the microswitch 56, permitting microswitch 56 in turn to be electrically connected to the combination switch and timer 58. The combination switch and timer 58 is also electrically connected by a conduit 62 to a plug 64 which can be connected to an electrical supply. Before current is directed to receptacle 54, it is necessary that the combined switch and timer be placed in an "on" position for a time period and the door 16 be closed, closing microswitch 56. This will direct current to receptacle 54 for the desired amount of time set by the timer and insure that the door 16 is closed.

For operation, the amalgam mixing device 22 is placed in the hood 14 on the heavy screen 20 and plugged into receptacle 54. When it is desired to actuate the amalgam mixing device 22, the door 16 is closed, electrically connecting the amalgam mixing device 22 to the combination switch and timer 58. Now, when this switch and timer is placed in an "on" position for a desired time period, the amalgam mixing device 22 will be electrically connected to the electrical supply, placing it into operation for that time period.

A switch 66 is located adjacent the combination switch and timer 58 and is electrically connected to the motor of the blower, or turbine, 11, by conduit 68. The switch 66 is also electrically connected by the conduit 62 to the plug 64. For operation, it can be seen that the blower, or turbine, 11, is merely turned on and off by the switch 66.

A switch 68 is located adjacent the other side of the combination switch and timer 58 and is electrically connected to the motor of the second suction producing device 44 by conduit 70. A switch 68 is also electrically connected by the conduit 62 to the plug 64. For operation, it can be seen that the second suction producing device 44 is merely turned on and off by the switch 68.

For other modes of operation, the door 16 and microswitch 56 could be removed, electrically connecting combination switch and timer 58 directly to receptacle 54 with the opening 52 closed, directing all of the air-flow into the hood 14 and over the amalgam mixing device 22 and through the heavy screen 20.

In another mode of operation, the combination switch and timer 56 could be electrically connected in series through switch 66 so that the amalgam mixing device 22 could not be turned on unless the switch 66 were placed in an on position, placing the blower, or turbine, 11 on. This would mean that for the amalgam mixing device 22 to operate when plugged into receptacle 54, the door 16 would have to be closed, placing the microswitch 56 in a "closed" position; that the combination switch and timer 58 be placed in an "on" position, selecting a time period; and the switch 66 be placed in an "on" position, actuating the motor of the blower, or turbine, 11.

An optional foot control 70 can be provided with foot pedals 66A, 58A and 68A, which can provide the functions of switch 66, combination switch and timer 58 and switch 68.

I claim:

1. A clean air device including a cabinet having a table top thereon, said table top having a large opening therein, a hood covering said large opening, said hood having an opening for directing flow thereinto, support means connected to said table top for supporting a contaminate producing device over said large opening, said cabinet having a first compartment and a second compartment located therein, said large opening on said table top being connected to said first compartment, first opening means connecting said first compartment and said second compartment, a suction producing device connected to said first opening means for drawing contaminate air through said large opening in said table top and said hood and directing it into said first opening means connecting said first compartment and said second compartment, said second compartment having second opening means connected to the exterior of said cabinet, filter means in said second opening means for filtering flow therethrough.

2. A clean air device as set forth in claim 1 wherein an electrical receptacle is located in said table top, a combination switch and timer means for directing a current to said receptacle for a predetermined amount of time, said combination switch and timer means having an "off" position and "on" position for directing current to said receptacle for a predetermined amount of time.

3. A clean air device as set forth in claim 2 wherein said cabinet contains a switch for turning said suction producing device "on" and "off", said switch is placed in series with said combination switch and timer means so that said current will not be directed to said receptacle unless said switch is placed in its "on" position placing said suction device on.

4. A clean air device as set forth in claim 2 wherein said hood opening has a door thereon for closing said opening, a microswitch located on said hood for contact by said door when it is closed, said microswitch being placed in an electrical series connection with said combination switch and timer means so that said current will not be directed to said receptacle by said switch and timer means unless said hood door is closed.

5. A clean air device as set forth in claim 4 wherein said cabinet contains a switch for turning said suction producing device "on" and "off", said switch is placed in series with said combination switch and timer means and said microswitch so that said current will not be directed to said receptacle by said switch and timer means unless said hood door is closed and said switch is placed in its "on" position placing said suction producing device on.

6. A clean air device as set forth in claim 1 wherein said filter means includes a high efficiency particle air filter and a charcoal filter.

7. A clean air device as set forth in claim 1 wherein an amalgam mixing device is positioned on said support means over said large opening in said table top, said amalgam mixing device being plugged into said electrical receptacle.

8. A clean air device as set forth in claim 1 wherein said first compartment also contains a second suction producing device, an oral cavity collector, said oral cavity collector being connected to said first compartment by a collecting hose, said hose being connected to said suction producing device for drawing contaminate air through said oral cavity collector and hose into said first compartment.

9. A clean air device as set in claim 1 wherein said support means is a heavy screen connected to said table top around said large opening.

* * * * *